United States Patent
Kaplin et al.

(10) Patent No.: US 9,737,552 B2
(45) Date of Patent: Aug. 22, 2017

(54) TREATMENT OF COGNITIVE IMPAIRMENT IN A SUBJECT WITH A NEUROLOGICAL AUTOIMMUNE DISEASE

(75) Inventors: Adam Kaplin, Baltimore, MD (US); Barbara S. Slusher, Kingsville, MD (US); Kristen A. Rahn, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/994,514

(22) PCT Filed: Dec. 14, 2011

(86) PCT No.: PCT/US2011/064920
§ 371 (c)(1),
(2), (4) Date: Sep. 11, 2013

(87) PCT Pub. No.: WO2012/082903
PCT Pub. Date: Jun. 21, 2012

(65) Prior Publication Data
US 2013/0344000 A1    Dec. 26, 2013

Related U.S. Application Data

(60) Provisional application No. 61/422,885, filed on Dec. 14, 2010.

(51) Int. Cl.
*A61K 31/662* (2006.01)
*A61K 49/06* (2006.01)
*A61K 31/19* (2006.01)
*A61K 31/66* (2006.01)

(52) U.S. Cl.
CPC ............ *A61K 31/662* (2013.01); *A61K 31/19* (2013.01); *A61K 31/66* (2013.01); *A61K 49/06* (2013.01)

(58) Field of Classification Search
None
See application file for complete search history.

(56) References Cited

U.S. PATENT DOCUMENTS

| | | | |
|---|---|---|---|
| 5,981,209 A | 11/1999 | Slusher et al. | |
| 6,348,464 B1 * | 2/2002 | Jackson et al. | 514/241 |
| 6,413,948 B1 | 7/2002 | Slusher et al. | |
| 2003/0013687 A1 | 1/2003 | Slusher | |
| 2004/0186081 A1 | 9/2004 | Slusher et al. | |
| 2005/0171065 A1 | 8/2005 | Jackson et al. | |
| 2007/0276021 A1 | 11/2007 | Delack | |

OTHER PUBLICATIONS

Brent GA. Clinical practice. Graves' disease. 2008 N. Engl. J. Med. 358: 2594-2605.*
Munoz et al. Apoptosis in the pathogenesis of systemic lupus erythematosus. 2008 Lupus 17: 371-375.*
Turner C. A review of myasthenia gravis: pathogenesis, clinical features and treatment. 2007 Curr. Anaesth. Crit. Care 18: 15-23.*
Tsukamoto et al. Progress in the discovery and development of glutamate carboxypeptidase II inhibitors. 2007 Drug Discov. Today 12: 767-776.*
Sajja et al. Proton magnetic resonance spectroscopy in multiple sclerosis. 2009 Neuroimaging Clin. N. Am. 19: 45-58.*
International Search Report for PCT/US2011/064920 dated Sep. 3, 2012.

* cited by examiner

*Primary Examiner* — Michael G Hartley
*Assistant Examiner* — Jennifer Lamberski
(74) *Attorney, Agent, or Firm* — Foley Hoag LLP (57) ABSTRACT

Described herein are methods for the treatment of cognitive impairment in a subject with a neurological autoimmune disease and methods for determining whether a subject who has a central nervous system autoimmune disease is likely to acquire a cognitive impairment.

8 Claims, 7 Drawing Sheets

TREATMENT OF COGNITIVE IMPAIRMENT IN A SUBJECT WITH A NEUROLOGICAL AUTOIMMUNE DISEASE

RELATED APPLICATIONS

This application is a National Stage Application of PCT/US11/64920 filed Dec. 14, 2011, which claims the benefit of U.S. Provisional Application No. 61/422,885, filed Dec. 14, 2010, the content of which is expressly incorporated by reference herein in its entirety.

BACKGROUND

Cognitive impairment is a comorbidity of many neurological diseases of the central nervous system, including multiple sclerosis. Multiple sclerosis affects over 2 million individuals worldwide. The most commonly and severely affected facets of cognition in multiple sclerosis patients are attention, anterograde episodic memory, processing speed, and visuospatial memory. Patients with progressive forms of multiple sclerosis are more commonly and severely affected by cognitive impairment than relapsing remitting multiple sclerosis patients, but overall disease severity has a very weak correlation with the presence of and/or severity of cognitive impairment.

A number of factors have been implicated as potentially contributing to cognitive impairment in multiple sclerosis patients, including global brain atrophy, genetic risk factors, dysregulated signaling pathways and accelerated inflammatory processes. However, the symptom variability in multiple sclerosis patients with cognitive impairment ranges from slight memory disturbances to complete dementia, and there is not a strong correlation between lesion load and the presence and/or severity of cognitive comorbities. These factors, combined with researchers' incomplete understanding of the molecular mechanisms behind cognitive impairment in neurological diseases, such as multiple sclerosis, have prevented the development of efficacious drug therapies.

The development of novel and effective treatments for cognitive impairment in MS could benefit over 1 million people worldwide. MS patients who are affected by cognitive impairment early in disease progression are more prone to severe learning and memory impairments later in life. The average age of MS onset is relatively young compared to other neurodegenerative disorders, approximately 20-40 years of age, and MS is the second leading cause of neurological disability in young adults in the United States. An estimated 50-80% of all MS patients are unemployed within 10 years of disease onset. Thus, early detection and treatment of cognitive impairment in MS would greatly improve the quality of life of many MS patients.

Thus, there exists a great need for diagnostic tests to identify neurological disease patients at risk for cognitive impairment and for novel compositions and methods for the treatment of cognitive impairment in neurological disease patients, such as patients with multiple sclerosis.

SUMMARY

Provided herein are novel methods for the treatment of cognitive impairment in subjects who have a central nervous system autoimmune disease (e.g., multiple sclerosis).

In some embodiments, the methods include administering the subject an inhibitor of glutamate carboxypeptidase II (GCPII).

In some embodiments of the methods described herein, any inhibitor of the activity and/or expression of GCPII can be used to treat cognitive impairment in subjects with a central nervous system autoimmune disease. In certain embodiments, for example, the GCPII inhibitor is a small molecule, an antibody, an inhibitory RNA molecule and/or a polypeptide. Thus, in some embodiments the inhibitor is a small molecule, such as 2-(phosphonomethyl)pentanedioic acid (2-PMPA) or 2-(3-mercaptopropyl)pentanedioic acid (2-MPPA). In some embodiments the inhibitor is an acid linked to a zinc binding group or a NAAG peptide analog.

In some embodiments, the subject that is being treated according to the methods described herein has multiple sclerosis. In some embodiments the brain of the subject or a region of the brain of the subject (e.g., the hippocampus or the frontal white matter) has reduced levels of N-acetylaspartylglutamate (NAAG). For example, in some embodiments the concentration of NAAG in the brain of the subject is less than 84% of the mean NAAG concentration found in individuals without cognitive impairment, or is less that 3.1 mM in the subject's hippocampus or less than 1.9 mM in the subject's frontal white matter.

In some embodiments, the methods described herein are used to treat a subject who has been diagnosed with a cognitive impairment. For example, in some embodiments, the cognitive impairment has been diagnosed using the Brief Repeatable Battery (BRB), the Minimal Assessment of Cognitive Function in MS (MACFIMS) battery or the Symbol Digit Modalities Test (SDMT), as described herein.

In certain embodiments, the methods described herein also include the step of determining the concentration of NAAG in the brain of the subject or in a region of the brain of the subject, such as in the hippocampus of the subject and/or in the frontal white matter of the subject. In some embodiments the level of NAAG in the brain of the subject or in a region of the brain of the subject is determined using magnetic resonance spectroscopy.

Provided herein are methods of determining whether a subject who has a central nervous system autoimmune disease (e.g., a subject with multiple sclerosis) is likely to acquire a cognitive impairment. In some embodiments the methods include the step of determining the concentration of NAAG in the brain of the subject or in a region of the brain of the subject (e.g., in the subject's hippocampus or frontal white matter). In some embodiments a level of NAAG in the brain of the subject or a region of the brain of the subject (e.g., in the hippocampus of the subject and/or in the frontal white matter of the subject) that is less than a control value indicates that the subject is likely to acquire a cognitive impairment. In some embodiments, the level of NAAG in the brain of the subject or a region of the brain of the subject is determined using magnetic resonance spectroscopy.

In some embodiments, the control value equal to the concentration of NAAG in the brain of a control subject or a region of the brain of a control subject (e.g., in the hippocampus of the control subject and/or in the frontal white matter of the control subject). In some embodiments, the control value is equal to 84% of the mean NAAG concentration found in the brain or in a region of the brain in individuals without cognitive impairment. In some embodiments, the control value is equal to 84% of the mean NAAG concentration found in the brain or in a region of the brain in individuals who have MS but who are not showing symptoms of cognitive impairment. In some embodiments the control value is 3.7 mM NAAG for the hippocampus or 2.2 mM NAAG for the frontal white matter.

In some embodiments, the diagnostic methods described herein also include the step of administering to the subject an inhibitor of GCPII if the subject is determined to be likely to acquire a cognitive impairment. In some embodiments the inhibitor of GCPII is an acid linked to a zinc binding group or a NAAG peptide analog. In certain embodiments the inhibitor of GCPII is 2-PMPA or 2-MPPA.

DETAILED DESCRIPTION

I. General

Provided herein are novel methods for the treatment of cognitive impairment in individuals suffering from a central nervous system (CNS) autoimmune disease such as multiple sclerosis (MS). Also provided herein are novel methods of determining whether an individual with a central nervous system autoimmune disease is likely to develop cognitive impairment.

N-acetylaspartylglutamate (NAAG), the most abundant neuropeptide in the mammalian brain, is a selective agonist for metabotropic glutamate receptor 3 (mGluR3), which inhibits glutamate release and negatively regulates brain cAMP and cGMP levels. NAAG has the following chemical structure:

NAAG is cleaved into N-acetyl-aspartate and glutamate by glutamate carboxypeptidase II (GCP II), also termed N-acetylated-α-linked acidic dipeptidase (NAALADase). GCPII is a membrane-bound enzyme expressed on the surface of CNS astrocytes. The amino acid sequences of the human isoforms of GCPII include those sequences cataloged in the NCBI database with GI numbers: 4758398, 62548858, 301500668, 301500666 and 301500670, each of which is herein incorporated by reference. The mRNA sequences of the human isoforms of GCPII include those sequences cataloged in the NCBI database with GI numbers: 4758397, 62548857, 301500667, 301500665 and 301500679, each of which is herein incorporated by reference.

As described herein, NAAG concentrations are reduced in the brains of MS patients compared to healthy controls and the level of NAAG in the brains of these MS patients correlates with their cognitive function. Specifically, MS patients with low brain NAAG concentrations have higher levels of cognitive impairment compared to MS patients with higher brain NAAG concentrations. What is more, upregulation of CNS NAAG concentration through inhibition of GCPII improves cognitive function in a mouse model of MS. In fact, in this model, both bong-term memory and fear memory are dramatically enhanced by administration of a GCPII inhibitor.

Thus, as described herein, since low brain NAAD concentrations correlate with poor cognitive performance in CNS autoimmune disease patients, determining whether a CNS autoimmune disease patient is likely to acquire cognitive impairment can be accomplished by measuring the concentration of NAAG in a part of his/her brain, such as the hippocampus or their frontal white matter. Conveniently, brain NAAD concentrations can be determined using techniques known in the art, such as through the use of magnetic resonance spectroscopy.

Furthermore, as described herein, cognitive impairment can be improved or prevented in CNS autoimmune patients through the administration of agents that inhibit the activity or expression of GCPII. A number of GCPII inhibitors are known in the art, including 2-(phosphonomethyl)pentanedioic acid (2-PMPA) or 2-(3-mercaptopropyl)pentanedioic acid (2-MPPA). Additional GCPII inhibitors useful in the methods described herein are provided below.

II. Definitions

As used herein, the term "administering" means providing a pharmaceutical agent (e.g. a GCPII inhibitor) or composition to a subject, and includes, but is not limited to, administering by a medical professional and self-administering.

The term "agent" is used herein to denote a chemical compound, a small molecule, a mixture of chemical compounds, a biological macromolecule (such as a nucleic acid, an antibody, a protein or portion thereof), or an extract made from biological materials such as bacteria, plants, fungi, or animal cells or tissues. Agents may be known in the art or identified as having a particular activity (e.g. inhibition of GCPII) by a screening assays described herein below. The activity of such agents may render them suitable as a "therapeutic agent" which is a biologically, physiologically, or pharmacologically active substance (or substances) that acts locally or systemically in a subject.

As used herein, the term "antibody" may refer to both an intact antibody and an antigen binding fragment thereof. Intact antibodies are glycoproteins that include at least two heavy (H) chains and two light (L) chains inter-connected by disulfide bonds. Each heavy chain includes a heavy chain variable region (abbreviated herein as VH) and a heavy chain constant region. Each light chain includes a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The term "antibody" includes, for example, monoclonal antibodies, polyclonal antibodies, chimeric antibodies, humanized antibodies, human antibodies, multispecific antibodies (e.g., bispecific antibodies), single-chain antibodies and antigen-binding antibody fragments. In certain embodiments, the antibodies described herein bind to the biologically active portion of GCPII.

"Biologically active portion of GCPII" refers to a portion of GCPII protein having a biological activity, such as the ability cleave NAAG into glutamate and N-acetyl-aspartate.

As used herein, the term "central nervous system autoimmune disease" or "CNS autoimmune disease" includes any disease or disorder in which a subject's immune system or a component of a subject's immune system mounts an immune response against the subject's own central nervous system or a component of the subject's own central nervous system. Examples of central nervous system autoimmune diseases include multiple sclerosis, Guillain-Barre syndrome, Lambert-Eaton myasthenic syndrome, myasthenia gravis, transverse myelitis, systemic lupus erythematosus (SLE or lupus), acute disseminated encephalomyelitis, vasculitis, Sjogren's syndrome, Graves' disease, autoimmune inner ear disease, narcolepsy, neuromyotonia, and schizophrenia.

As used herein, the term "cognitive impairment" includes any clinical dysfunction of cognitive ability in a subject, including impairment of attention, processing, reasoning, memory, verbal fluency and/or visuospatial perception. Tests for identifying cognitive impairment include the Brief Repeatable Battery (BRB), Minimal Assessment of Cognitive Function in MS (MACFIMS) battery and the Symbol Digit Modalities Test (SMDT). Tests for cognitive impairment are described, for example, in Rao, S. M., *A Manual for the Brief Repeatable Battery of Neuropsychological Tests in Multiple Sclerosis*. Wilwaukee: Medical College of Wisconsin; 1998; Strober et al., *Mult. Scler.* 15:1077-1084 (2009) and Morrow et al., *Mult. Scler.* 16:1385-1392 (2010), each of which is hereby incorporated by reference in its entirety.

The term "control" includes any portion of an experimental system designed to demonstrate that the factor being tested is responsible for the observed effect, and is therefore useful to isolate and quantify the effect of one variable on a system. For example, in certain embodiments of the methods described herein, the concentration of NAAG in the brain of a subject is compared to a control value. Such a control value can be, for example, the concentration of NAAG in the brain of a control subject (e.g., a subject who does not have cognitive impairment), the mean or median concentration of NAAG in the brains of a plurality of control subjects, or can be a specific value, such as a concentration of 3.1 mM in the hippocampus or 1.9 mM in the frontal white matter.

As used herein, an "effective amount" is an amount effective for improving or preventing cognitive impairment. Thus, in certain embodiments a subject is administered an effective amount of a GCPII inhibitor.

The term "GCPII inhibitor" or "agent that inhibits GCPII" refers to an agent that decreases the ability of a GCPII to cleave NAAG into N-acetyl-aspartate and glutamate and/or decreases the level of GCPII protein. In some embodiments the GCPII inhibitor has an $IC_{50}$ if less than 1 µM, 500 nM, 250 nM, 200 nM, 150 nM, 100 nM, 75 nM, 50 nM or 25 nM. In some embodiments, a GCPII inhibitor may decreases the cellular level of a GCPII protein by at least about 10%, 25%, 50%, 75%, 90% or 95%.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" is art-recognized and refers to the relatively non-toxic, inorganic and organic acid addition salts of compounds, including, for example, those contained in compositions described herein.

The terms "polynucleotide" and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. The term "recombinant" polynucleotide means a polynucleotide of genomic, cDNA, semisynthetic, or synthetic origin which either does not occur in nature or is linked to another polynucleotide in a non-natural arrangement.

The term "small molecule" is art-recognized and refers to a composition which has a molecular weight of less than about 2000 amu, or less than about 1000 amu, and even less than about 500 amu.

As used herein, the term "subject" refers to a mammal, e.g., a human, mouse, rat, guinea pig, dog, cat, horse, cow, pig, or non-human primate, such as a monkey, chimpanzee, baboon or rhesus. In some embodiments, the subject is a human.

The phrases "therapeutically-effective amount" and "effective amount" as used herein means that amount of a compound, material, or composition comprising a compound described herein which is effective for producing some desired therapeutic effect in at least a sub-population of cells in an animal at a reasonable benefit/risk ratio applicable to any medical treatment.

As used herein, the term "treating" a disease or disorder in a subject includes both therapeutic treatment and prophylactic treatment. Thus, a subject can be treated for a disorder, for example, if the subject has the disorder, if the subject is suspected of having the disorder, and/or if the subject is predisposed towards acquiring the disorder.

III. GCPII Inhibitors

In certain embodiments, described herein are methods of treating cognitive impairment by administering to a subject an agent that inhibits GCPII. Agents that may be used for the inhibition of GCPII include, for example, small molecules, inhibitory nucleic acids (e.g., siRNA or shRNA molecules specific for GCPII mRNA), antibodies (e.g., antibodies that bind to GCPII protein) and polypeptides (e.g., polypeptides that bind to the biologically active portion of the GCPII protein).

In some embodiments, any agent that inhibits GCPII can be used to practice the methods described herein. Such agents can be those described herein, those known in the art, or those identified through routine screening assays (e.g. the screening assays described herein).

In some embodiments, assays used to identify agents useful in the methods of the described herein include a reaction between GCPII and one or more assay components. The other components may be either a test agent (e.g. the potential agent), or a combination of test agents and NAAG. Agents identified via such assays, may be useful, for example, for treating cognitive impairment according to the methods described herein.

Agents useful in the methods described herein may be obtained from any available source, including systematic libraries of natural and/or synthetic compounds. Agents may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of agents may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

Agents useful in the methods described herein may be identified, for example, using assays for screening candidate or test agents which inhibit the activity of GCPII. For example, candidate or test agents can be screened for the ability to inhibit the cleavage of NAAG by GCPII.

The basic principle of the assay systems used to identify agents that inhibit the activity of GCPII involves preparing a reaction mixture containing GCPII and NAAG under conditions and for a time sufficient to allow GCPII to cleave NAAG into NAA and glutimate. In order to test an agent for modulatory activity, the reaction mixture is prepared in the presence and absence of the test agent. The test agent can be initially included in the reaction mixture, or can be added at a time subsequent to the addition of GCPII and NAAG. Control reaction mixtures are incubated without the test agent or with a placebo. The cleavage of NAAG by GCPII is then detected using standard methodologies. For example, disappearance of NAAG and/or the formation of NAA or glutamate can be measured in the sample using mass spectrometry or liquid chromatography. The cleavage activity in the control reaction, but less or no such cleavage in the reaction mixture containing the test agent, indicates that the agent inhibits the activity of GCPII.

Modulators of GCPII expression may also be identified, for example, using methods wherein a cell that expresses GCPII is contacted with a candidate agent and the expression of GCPII mRNA or protein is determined using standard methods known in the art. The level of expression of mRNA or protein in the presence of the candidate agent is compared to the level of expression of mRNA or protein in the absence of the candidate agent. The candidate agent can then be identified as an inhibitor of GCPII expression based on this comparison.

Small Molecule Inhibitors

In certain embodiments, described herein are methods for the treatment of cognitive impairment through the administration of small molecule inhibitors of GCPII. Exemplary GCPII inhibitors are described in, for example, U.S. Pat. Nos. 5,880,112; 5,968,915; 6,025,344; 6,384,022; 6,348,464; 7,148,250 and U.S. Patent Pub. Nos. 2006/0135812; 2005/0080139, each of which is incorporated by reference in its entirety.

In certain embodiments, the GCPII inhibitor is a non-hydrolyzable or conformationally restricted NAAG peptide analogs, glutamate derivative and/or quisqualic acid. In certain embodiments the GCPII inhibitor includes a glutarate moiety to bind to the C-terminal glutamate recognition site of GCPII and a zinc chelating group to coordinate the divalent zinc atoms at the enzyme's active site. Thus, in some embodiments, the inhibitor is an acid linked to a zinc binding group or a NAAG peptide analog.

In some embodiments, the GCPII inhibitor is a phosphate-base inhibitor such as 2-(phosphonomethyl)pentanedioic acid (2-PMPA), GPI-5232 or VA-033. The structures and inhibitory activity of 2-PMPA, GPI-5232 and VA-033 are provided below.

2-PMPA

IC$_{50}$ 0.3 nM

GPI-5232

82 nM

VA-033

12 nM

In some embodiments the GCPII inhibitor is a thiol-based inhibitor, such as 2-(3-mercaptopropyl)pentanedioic acid) (2-MPPA). The structures and inhibitory activity of exemplary thiole-based GCPII inhibitors are provided below.

2-MPPA

IC$_{50}$ 90 nM

6c

IC$_{50}$ 15 nM

17

IC$_{50}$ 22 nM

26a

IC$_{50}$ 14 nM

26b

IC$_{50}$ 32 nM

In some embodiments, the GCPII inhibitor is a urea-based inhibitor, such as ZJ-43. The structures and inhibitory activity of exemplary urea-based inhibitors are provided below.

Inhibitory RNA Molecules

In certain embodiments, the CPGII inhibiting agent is an inhibitory RNA molecules that specifically target GCPII mRNA (e.g., antisense molecules, siRNA or shRNA molecules, ribozymes or triplex molecules).

The inhibitory RNA molecules described herein may be administered to a subject or constructs encoding such molecules may be administered to a subject. Antisense constructs, antisense oligonucleotides, RNA interference constructs or siRNA duplex RNA molecules can be used to interfere with expression of a protein of interest, e.g., a GCPII protein. Typically at least 15, 17, 19, or 21 nucleotides of the complement of the GCPII mRNA sequence are sufficient for an antisense molecule. Typically at least 19, 21, 22, or 23 nucleotides of a target sequence are sufficient for an RNA interference molecule. The RNA interference molecule may have a 2 nucleotide 3' overhang. If the RNA interference molecule is expressed in a cell from a construct, for example from a hairpin molecule or from an inverted repeat of the desired GCPII sequence, then the endogenous cellular machinery will create the overhangs. Inhibitory RNA molecules can be prepared by chemical synthesis, in vitro transcription, or digestion of long dsRNA by Rnase III or Dicer.

These can be introduced into cells by transfection, electroporation, or other methods known in the art. See Hannon, G J, 2002, RNA Interference, Nature 418: 244-251; Bernstein E et al., 2002, The rest is silence. RNA 7: 1509-1521; Hutvagner G et al., RNAi: Nature abhors a double-strand. Curr. Opin. Genetics & Development 12: 225-232; Brummelkamp, 2002, A system for stable expression of short interfering RNAs in mammalian cells. Science 296: 550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. Nature Biotechnol. 20:500-505; Miyagishi M, and Taira K. (2002). U6-promoter-driven siRNAs with four uridine 3' overhangs efficiently suppress targeted gene expression in mammalian cells. Nature Biotechnol. 20:497-500; Paddison P J, Caudy A A, Bernstein E, Hannon G J, and Conklin D S. (2002). Short hairpin RNAs (shRNAs) induce sequence-specific silencing in mammalian cells. Genes & Dev. 16:948-958; Paul C P, Good P D, Winer I, and Engelke D R. (2002). Effective expression of small interfering RNA in human cells. Nature Biotechnol. 20:505-508; Sui G, Soohoo C, Affar E-B, Gay F, Shi Y, Forrester W C, and Shi Y. (2002). A DNA vector-based RNAi technology to suppress gene expression in mammalian cells. Proc. Natl. Acad. Sci. USA 99(6):5515-5520; Yu J-Y, DeRuiter S L, and Turner D L. (2002). RNA interference by expression of short-interfering RNAs and hairpin RNAs in mammalian cells. Proc. Natl. Acad. Sci. USA 99(9):6047-6052.

In the present methods, an inhibitory RNA molecule or an inhibitory RNA encoding polynucleotide can be administered to the subject, for example, as naked RNA, in combination with a delivery reagent, and/or as a nucleic acid comprising sequences that express the siRNA or shRNA molecules. In some embodiments the nucleic acid comprising sequences that express the siRNA or shRNA molecules are delivered within vectors, e.g. plasmid, viral and bacterial vectors. Any nucleic acid delivery method known in the art can be used in the methods described herein. Suitable delivery reagents include, but are not limited to, e.g, the Minis Transit TKO lipophilic reagent; lipofectin; lipofectamine; cellfectin; polycations (e.g., polylysine), atelocollagen, nanoplexes and liposomes. The use of atelocollagen as a delivery vehicle for nucleic acid molecules is described in Minakuchi et al. Nucleic Acids Res., 32(13): e109 (2004); Hanai et al. Ann NY Acad. Sci., 1082:9-17 (2006); and Kawata et al. Mol Cancer Ther., 7(9):2904-12 (2008); each of which is incorporated herein in their entirety.

In some embodiments of the methods described herein, liposomes are used to deliver an inhibitory oligonucleotide to a subject. Liposomes suitable for use in the methods described herein can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), Ann. Rev. Biophys. Bioeng. 9:467; and U.S. Pat. Nos. 4,235,871, 4,501,728, 4,837,028, and 5,019,369, the entire disclosures of which are herein incorporated by reference.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure.

Opsonization-inhibiting moieties for use in preparing the liposomes described herein are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is herein incorporated by reference.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethyleneglycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes."

Antibodies

In certain embodiments, the inhibitory agent used in the methods described herein is an antibody binds specifically to GCPII. Such antibodies can be polyclonal or monoclonal and can be, for example, murine, chimeric, humanized or fully human.

Polyclonal antibodies can be prepared by immunizing a suitable subject (e.g. a mouse) with a polypeptide immunogen (e.g., a GCPII protein or fragment thereof). The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by known techniques, such as protein A chromatography, to obtain the IgG fraction.

At an appropriate time after immunization, e.g., when the antibody titers are highest, antibody-producing cells can be obtained from the subject and used to prepare monoclonal antibodies using standard techniques, such as the hybridoma technique originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques, all of which are incorporated by reference herein. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

As an alternative to preparing monoclonal antibody-secreting hybridomas, a monoclonal specific for GCPII can be identified and isolated by screening a recombinant combinatorial immunoglobulin library (e.g., an antibody phage display library or an antibody yeast display library) with the appropriate polypeptide (e.g. a polypeptide fragment of GCPII) to thereby isolate immunoglobulin library members that bind the polypeptide.

Additionally, recombinant antibodies specific for GCPII, such as chimeric or humanized monoclonal antibodies, can be made using standard recombinant DNA techniques. Such chimeric and humanized monoclonal antibodies can be produced by recombinant DNA techniques known in the art, for example using methods described in U.S. Pat. No. 4,816,567; U.S. Pat. No. 5,565,332; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060, all of which are incorporated by reference herein.

Human monoclonal antibodies specific for GCPII can be generated using transgenic or transchromosomal mice carrying parts of the human immune system rather than the mouse system. For example, "HuMAb mice" which contain a human immunoglobulin gene miniloci that encodes unrearranged human heavy ($\mu$ and $\gamma$) and $\kappa$ light chain immunoglobulin sequences, together with targeted mutations that inactivate the endogenous $\mu$ and $\kappa$ chain loci (Lonberg, N. et al. (1994) Nature 368(6474): 856 859). Accordingly, the mice exhibit reduced expression of mouse IgM or $\kappa$, and in response to immunization, the introduced human heavy and light chain transgenes undergo class switching and somatic mutation to generate high affinity human IgG$\kappa$ monoclonal antibodies (Lonberg, N. et al. (1994), supra; reviewed in Lonberg, N. (1994) Handbook of Experimental Pharmacology 113:49 101; Lonberg, N. and Huszar, D. (1995) Intern. Rev. Immunol. Vol. 13: 65 93, and Harding, F. and Lonberg, N. (1995) Ann. N.Y. Acad. Sci. 764:536 546). The preparation of HuMAb mice is described in Taylor, L. et al. (1992) Nucleic Acids Research 20:6287 6295; Chen, J. et al. (1993)

International Immunology 5: 647 656; Tuaillon et al. (1993) Proc. Natl. Acad. Sci. USA 90:3720 3724; Choi et al. (1993) Nature Genetics 4:117 123; Chen, J. et al. (1993) EMBO J. 12: 821 830; Tuaillon et al. (1994) J. Immunol. 152:2912 2920; Lonberg et al., (1994) Nature 368(6474): 856 859; Lonberg, N. (1994) Handbook of Experimental Pharmacology 113:49 101; Taylor, L. et al. (1994) International Immunology 6: 579 591; Lonberg, N. and Huszar, D. (1995) Intern. Rev. Immunol. Vol. 13: 65 93; Harding, F. and Lonberg, N. (1995) Ann. N.Y. Acad. Sci. 764:536 546; Fishwild, D. et al. (1996) Nature Biotechnology 14: 845 851. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807.

In certain embodiments, the antibodies described herein are able to bind to GCPII with a dissociation constant of no greater than $10^{-6}$, $10^{-7}$, $10^{-8}$ or $10^{-9}$ M. Standard assays to evaluate the binding ability of the antibodies are known in the art, including for example, ELISAs, Western blots and RIAs. The binding kinetics (e.g., binding affinity) of the antibodies also can be assessed by standard assays known in the art, such as by Biacore analysis. In some embodiments, the binding of the antibody to GCPII substantially inhibits the cleavage of NAAG by GCPII. As used herein, an antibody substantially inhibits the cleavage of NAAG by GCPII when an excess of antibody reduces the rate of NAAG cleavage by at least about 20%, 40%, 60% or 80%, 85% or 90%.

IV. Pharmaceutical Compositions

The agents described herein (e.g. agents that inhibit GCPII) can be incorporated into pharmaceutical compositions suitable for administration to a subject. The compositions may contain a single such agent or any combination of inhibitory agents described herein and a pharmaceutically acceptable carrier. The pharmaceutical composition may further comprise additional agents useful for treating MS or cognitive impairment.

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition described herein is formulated to be compatible with its intended route of administration. Examples of routes of administration include intravenous, oral, and nasal administration.

Toxicity and therapeutic efficacy of the agents described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods described herein, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

Appropriate doses agents depends upon a number of factors within the scope of knowledge of the ordinarily skilled physician, veterinarian, or researcher. The dose(s) of the small molecule will vary, for example, depending upon the identity, size, and condition of the subject or sample being treated, further depending upon the route by which the composition is to be administered.

V. Methods of Treatment

Described herein are novel methods for the treatment of cognitive impairment in a subject (e.g., a subject in need thereof) who has a CNS autoimmune disease (e.g., multiple sclerosis).

Examples of CNS autoimmune diseases include, for example, multiple sclerosis, Guillain-Barre syndrome, Lambert-Eaton myasthenic syndrome, myasthenia gravis, transverse myelitis, systemic lupus erythematosus (SLE or lupus), acute disseminated encephalomyelitis, vasculitis, Sjogren's syndrome, Graves' disease, autoimmune inner ear disease, narcolepsy, neuromyotonia, and schizophrenia.

In some embodiments, the CNS autoimmune disease is multiple sclerosis (MS). MS is an autoimmune disease often characterized by recurrent episodes of demyelination and inflammation within the central nervous system. Symptoms of MS can include changes in sensation (e.g. hypoesthesias and paraesthesias), muscle weakness, muscle spasms, difficulty moving; difficulty with coordination and/or balance (e.g. ataxia); difficulty speaking (e.g. dysarthria), difficulty swallowing (e.g. dysphagia), difficulty controlling eye movement (e.g. nystagmus), impaired vision (e.g. diplopia), fatigue, pain (e.g. acute or chronic), difficulty controlling bladder function, difficulty controlling bowel function, and/or depression.

A subject in need thereof may include, for example, a subject who has been diagnosed with multiple sclerosis, a subject who has been diagnosed with cognitive impairment, a subject who is likely to acquire cognitive impairment, a subject with reduced levels of NAAG in their brain (or a portion of their brain, such as their hippocampus or frontal white matter), and/or a subject with increased levels of glutamate in their brain (or a portion of their brain, such as their hippocampus or frontal white matter). A subject in need thereof may also include, for example, a subject who has been determined to have an increased likelihood of acquiring a cognitive impairment by the methods described herein. For example, in some embodiments the level of NAAG in the brain of the subject is less than 84% of the mean NAAG level found in individuals without cognitive impairment, or is less that 3.1 mM in the subject's hippocampus or less than 1.9 mM in the subject's frontal white matter.

In certain embodiments, the subject has been diagnosed with a cognitive impairment. Cognitive impairment includes any clinical dysfunction of cognitive ability in a subject, including impairment of attention, processing, reasoning, memory, verbal fluency and/or visuospatial perception. Tests for identifying cognitive impairment include the Brief Repeatable Battery (BRB), Minimal Assessment of Cognitive Function in MS (MACFIMS) battery and the Symbol Digit Modalities Test (SMDT). Tests for cognitive impairment are described, for example, in Rao, S. M., *A manual for the Brief Repeatable Battery of Neuropsychological Tests in multiple sclerosis. Wilwaukee: Medical College of Wisconsin;* 1998; Strober et al., *Mult. Scler.* 15:1077-1084 (2009) and Morrow et al., *Mult. Scler.* 16:1385-1392 (2010), each of which is hereby incorporated by reference in its entirety.

For example, in certain embodiments, the presence of a cognitive impairment in the subject is determined as follows. The cognitive impairment index (CII) provides a composite measure of cognitive dysfunction. For each subject, a grading quotient is applied to each of the measures, based on the number of standard deviations (SD) of a control mean value. For each test (i), a grade 0 is given if the subject scored at Si<1 SD, a grade 1 is given if the subject scored between 1 SD and 2 SDs, a grade of 2 is given if the subject scored between 2 SD and 3 SDs, and so on. A CII is obtained for each cognitive domain (general intellectual functioning, memory, attention/speed of information processing, executive functions and language) by averaging all the grades obtained in the corresponding tests (Sum of Si/number of test). Thus, six CIIs are obtained: one for each cognitive domain and one corresponding to the mean of these CIIs providing a global measure of cognitive dysfunction (overall CII). At baseline, CIIs are computed for each subject using the mean and SD values obtained in controls at baseline. Subjects are classified as cognitively impaired if they obtain, for at least one domain, a CII grading at or above 2. This definition of cognitive impairment can be applied to, for example, the Brief Repeatable Battery (BRB) for MS or the Minimal Assessment of Cognitive Function in MS (MACFIMS), among other cognitive batteries. Alternatively, subjects are considered cognitively impaired if they performed one and a half standard deviations below controls on two or more MACFIMS variables or if their total score on the Symbol Digit Modalities Test (SDMT) of 55 or lower.

In some embodiments of the methods described herein, a pharmaceutical composition described herein is administered to the subject. In some embodiments, pharmaceutical composition can include any inhibitor of the activity and/or expression of GCPII. In certain embodiments, for example, the GCPII inhibitor is a small molecule (e.g., 2-PMPA or 2-MPAA), an antibody (e.g., an antibody that binds to GCPII), an inhibitory RNA molecule (e.g., an RNAi molecule or an siRNA molecule) and/or a polypeptide. In some embodiments the inhibitor is an acid linked to a zinc binding group or a NAAG peptide analog.

In some embodiments, the pharmaceutical composition described herein will incorporate the therapeutic agent to be delivered in an amount sufficient to deliver to a patient a therapeutically effective amount of an incorporated therapeutic agent or other material as part of a prophylactic or therapeutic treatment. The desired concentration of the active agent will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Actual dosage levels of the active ingredients in the pharmaceutical compositions described herein may be varied so as to obtain an amount of the active agent which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

In certain embodiments, the methods described herein also include the step of determining the level of NAAG in the brain of the subject (e.g., in the hippocampus of the subject and/or in the frontal white matter of the subject). For example, in some embodiments the level of NAAG in the brain of the subject is determined using magnetic resonance spectroscopy.

VI. Diagnostic Methods

Provided herein are methods of determining whether a subject who has a central nervous system autoimmune disease (e.g., a subject with multiple sclerosis) is likely to acquire a cognitive impairment.

In some embodiments the methods include determining the level of NAAG in the brain of the subject or in a particular region of the brain of the subject. For example, in some embodiments the level of NAAG in the frontal cortex, the hippocampus, the cerebellum and/or the frontal white matter of the subject. The concentration of NAAG in the brain or region of the brain in the subject can be determined using any method known in the art. For example, the levels of NAAG can be determined using magnetic resonance spectroscopy. Use of magnetic resonance spectroscopy to determine CNS NAAG concentrations is described, for example, in Prescot et al., *Mol. Pain.* 5:34 (2009) and McIntyre et al., *J. Magn. Reson. Imaging* 26:1596-1606 (2007), each of which is incorporated by reference in its entirety.

In some embodiments a level of NAAG in the brain of the subject or a region of the brain of the subject (e.g., in the hippocampus of the subject and/or in the frontal white matter of the subject) that is less than a control value indicates that the subject is likely to acquire a cognitive impairment. In some embodiments, the control value is a value equal to the level of NAAG in the brain of a control subject or in a region of the brain of a control subject (e.g., in the hippocampus of the control subject and/or in the frontal white matter of the control subject). In some embodiments, the control value is the level of NAAG in the brain of the subject is less than 90%, 89%, 88%, 87%, 86%, 85%, 84%, 83%, 82%, 81% or 80% of the mean NAAG level found in individuals without cognitive impairment. In some embodiments the control value is 3.7 mM NAAG for the hippocampus or 2.2 mM NAAG for the frontal white matter.

In some embodiments, the methods described herein also include administering to the subject an inhibitor of GCPII if the subject is likely to acquire a cognitive impairment (e.g., also performing a therapeutic method described herein).

The methods described herein are further illustrated by the following examples which should not be construed as limiting. The contents of all references, patents and published patent applications cited throughout this application, as well as the Figures, are incorporated herein by reference.

EXAMPLES

Figure 1:
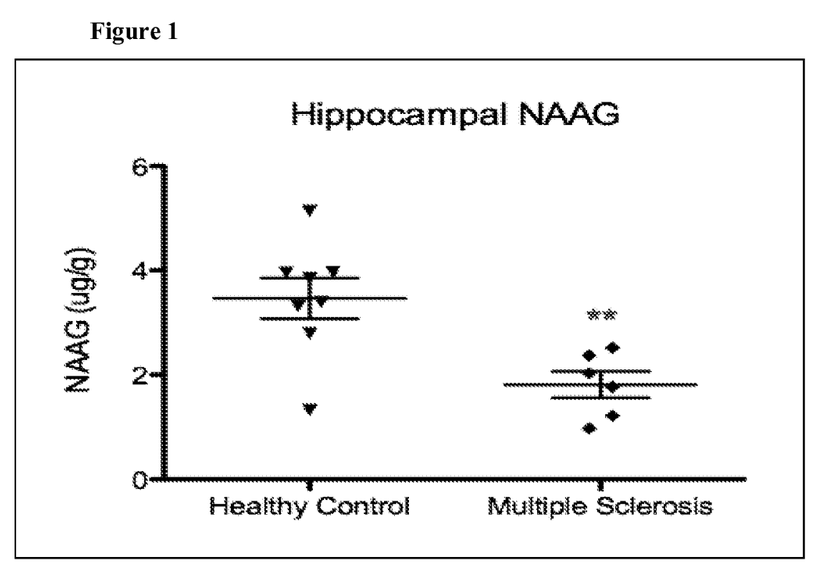
FIG. 1 shows magnetic resonance spectroscopy data that demonstrate a decreased concentration of NAAG in the left hippocampus of multiple sclerosis patients compared to healthy controls. Values represent mean±SEM. n=10 mice/group. Significantly different from healthy controls at p<0.01 (**).
Figure 2:
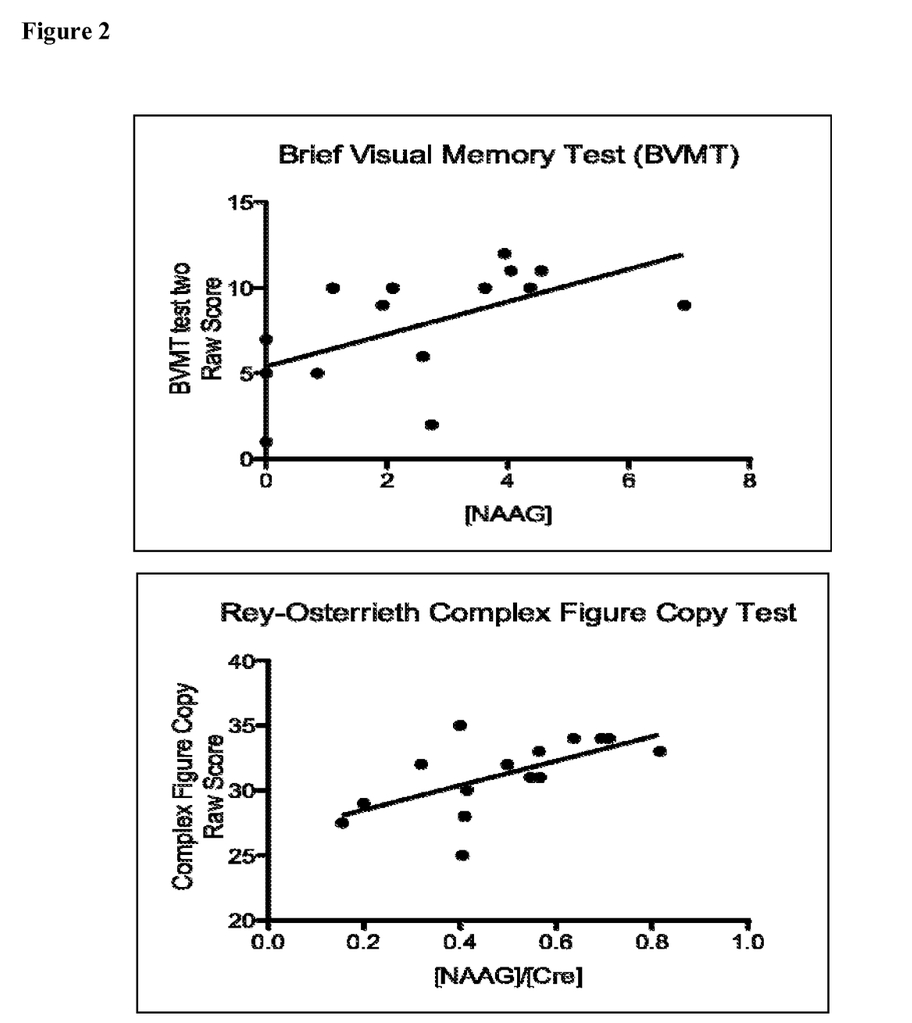
FIG. 2 shows magnetic resonance spectroscopy data from MS patients that demonstrate a correlation between NAAG levels in the right hippocampus and performance on two cognitive tasks.

Example 1: Hippocampal NAAG Levels Correlate with Cognitive Impairment in Subjects with Multiple Sclerosis To determine if any differences in brain metabolite concentrations exist between MS patients and healthy control subjects and to measure this relationship to cognitive function, a cognitive test battery and magnetic resonance spectroscopy (MRS) studies were conducted. Healthy volunteers and newly diagnosed MS patients who had no previous exposure to disease-modifying drugs underwent MRS and cognitive testing. MRS studies revealed a difference in hippocampal NAAG concentration between MS patients and age-matched healthy control subjects. Specifically that MS patients have decreased hippocampal NAAG compared to control subjects (FIG. 1). MS patient performance on the cognitive battery varied, indicating cognitive impairment in some individuals and preserved cognitive function in others. The concentration of hippocampal NAAG correlated to the subject's performance on two cognitive tests, the Brief Visual Memory Test and the Rey-Osterrieth Complex Figure Copy Test (FIG. 2).

Figure 3:
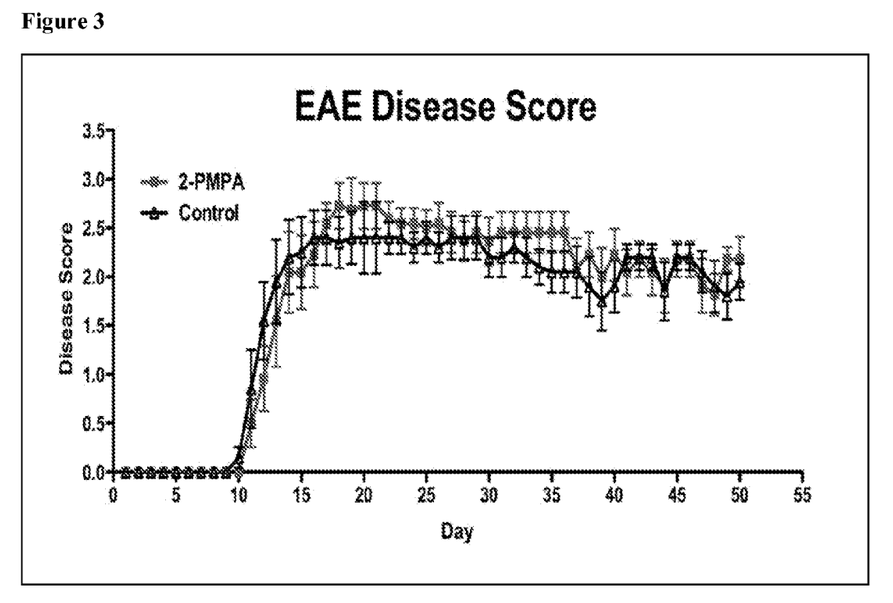
FIG. 3 shows that mice immunized with MOG 35-55 developed EAE 10-12 days post-immunization. Mice were treated with either Vehicle or 2-PMPA for the duration of the experiment and assigned daily disease scores based on the 0-6 behavior scale. Values represent mean±SEM. n=10 mice/group.

Example 2: GCPII Inhibition Improves Cognitive Function in an Animal Model of Multiple Sclerosis The effects of GCPII inhibition were tested on an animal model of multiple sclerosis (experimental autoimmune encephalomyelitis, or "EAE"). To induce EAE, mice were given two 50 µL subcutaneous flank injections of myelin oligodendrocyte glycoprotein 35-55 peptide fragment ($MOG_{35-55}$) dissolved in 50 µL PBS emulsified in 50 µL IFA supplemented with 400 µg M. tuberculosis H37Ra, at a final concentration of 100 µg $MOG_{35-55}$ per 100 µL total volume. At the time of MOG immunization and 2 days later, all EAE mice were administered intraperitoneal injections of 300 ng pertussis toxin in 100 µL PBS. Immunized mice were treated with either 2-PMPA or a vehicle control for the duration of the experiment. Vehicle (50 mM HEPES buffer) or 2-PMPA (100 mg/kg in vehicle at a pH of 7.4) was delivered daily via 0.1 mL intraperitoneal injections from the time of EAE immunization until sacrifice. Mice developed signs of EAE approximately 10 days post-immunization. Disease severity and progression, as measured by EAE disease scores, did not differ between 2-PMPA and Control mice for the duration of the experiment (FIG. 3). This indicates that 2-PMPA does not affect physical signs of EAE disease.

To measure cognitive function in EAE mice, Barnes maze testing was conducted using the immunized mice, beginning approximately 4 weeks post-immunization. The Barnes maze is a land maze that does not require dietary restrictions, electric footshock, or high velocity, thereby minimizing the stress placed on EAE mice. Animals were trained on the Barnes maze (AccuScan Instruments, Columbus, Ohio) for 4 trials per day (inter-trial interval >30 minutes) for 4 consecutive days. Briefly, mice were placed in the center of the maze platform under an opaque enclosed 3"×5"× container. After 15 seconds the container was removed and the mice were free to move in the maze. A target box was placed under 1 of the 40 holes around the maze perimeter, and the location of the target box, along with the location of 4 equally spaced polarizing visual cues and one lamp, remained the same throughout all trials. Mice were given up to 3 minutes to locate and enter the target box, and were gently guided into the target box if it was not found within the 3 minute limit. Following entry into the target box, the box was covered and the mouse remained in the box for 30 seconds before transfer to a holding cage. Paths were recorded and latency to the target hole, path efficiency, speed, and directional times were calculated using ANY-maze software (Stoelting, Wood Dale, Ill.).

Figure 4:
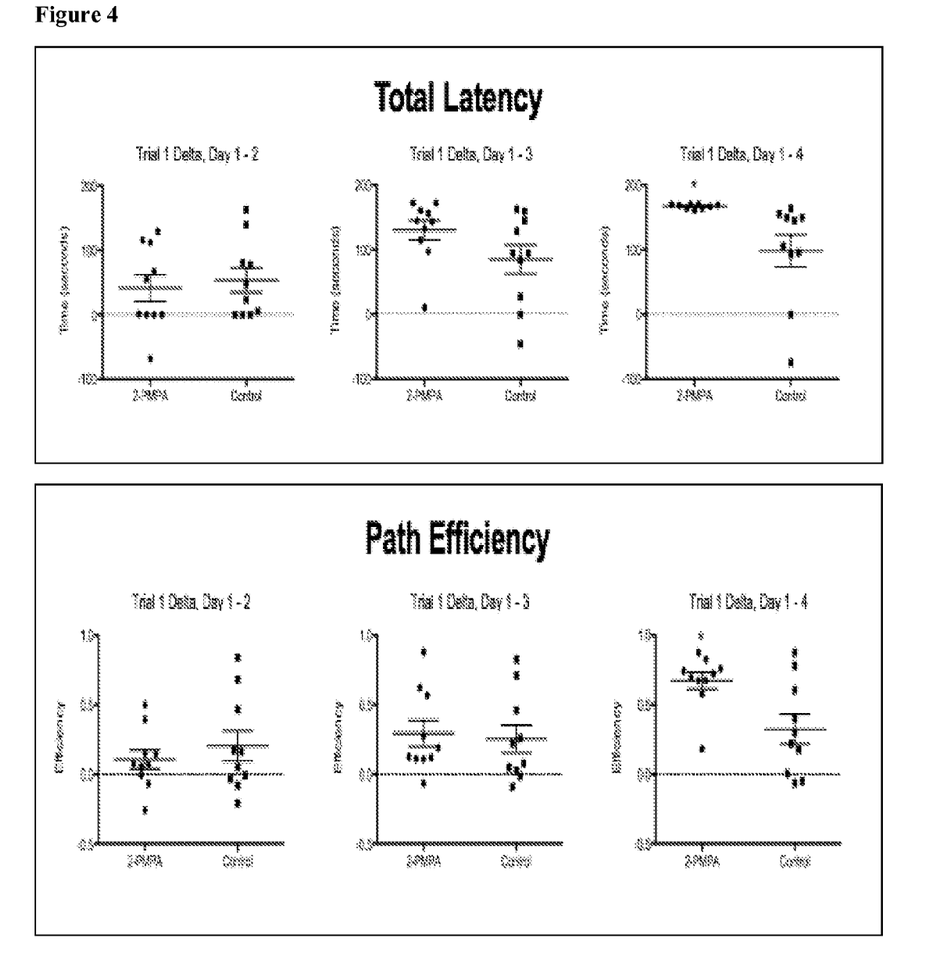
FIG. 4 shows Barnes maze data that depict the first trial of day 2, 3, or 4 subtracted from the first trial of day 1 of Barnes maze testing. Results depict total latency (A), and path efficiency (B). Values represent mean±SEM. Significantly different from Control at p<0.05 (*).

EAE mice treated with 2-PMPA or vehicle demonstrated equal baseline performances on the Barnes maze, with only 1 mouse per group entering the target box on the first trial of the first day within the 3 minute limit. Both treatment groups demonstrated similar initial learning abilities, with mean primary latency (time before head poke into target box), total latency (time before entry into the target box), and path efficiency (total distance traveled on maze/distance from starting point to target box) equal between groups on the first two days of Barnes maze testing. Trends towards improved performance in 2-PMPA-treated mice emerged on day 3, and a significant separation in performance between 2-PMPA treated and control mice was observed on day 4. When comparing performance between the first trial of day 4 to baseline (day 1, trial 1), 2-PMPA mice had a significant improvement compared to Control mice in primary latency (Mean±SEM: 167.4±1.187 vs. 134.0±10.30, respectively; p=0.0072), total latency (Mean±SEM: 167.4±1.187 vs. 98.42±24.66, respectively; p=0.0171), and path efficiency (Mean±SEM: −0.7276±0.0295 vs. −0.3235±0.107, respectively; p=0.0029) (FIG. 4).

Comparison of back-to-back Barns maze trials on consecutive days (e.g. trial 4 of day 3 vs. trial 1 of day 4) is an indication of long-term memory in mice. As demonstrated herein, 2-PMPA enhances long-term memory in EAE mice, significantly decreasing total latency (Mean±SEM: 13.14±7.69 vs. −38.82±19.04, respectively; p=0.021) and increasing path efficiency (Mean±SEM: −0.1377±0.0937 vs. 0.2087±0.0983, respectively; p=0.020) compared to controls. No differences were observed between 2-PMPA and control EAE groups with regard to maximum speed in the maze, supporting the finding that physical disability did not differ between 2-PMPA and control mice as measured by EAE disease score.

To measure fear memory and amygdala function in EAE mice, fear conditioning tests were performed. Following the Barnes maze testing, animals were given 1-2 weeks rest then subjected to fear conditioning. Briefly, animals were placed in a fear conditioning chamber for 240 seconds on 3 consecutive days. On day 1, a 2000 Hz tone was played for 28 seconds (seconds 180-208), immediately followed by a 2 second scrambled footshock (seconds 208-210). On day 2, animals were placed back in the same testing environment, but neither sound nor shock was administered. On days 3 and 5, mice were placed in a novel wooden box inside the fear conditioning chamber, and a 2000 Hz tone was played for 120 seconds (seconds 121-240). The duration of freezing behavior on each day was measured using FreezeScan software (Clever Sys Inc., Reston, Va.).

Figure 5:
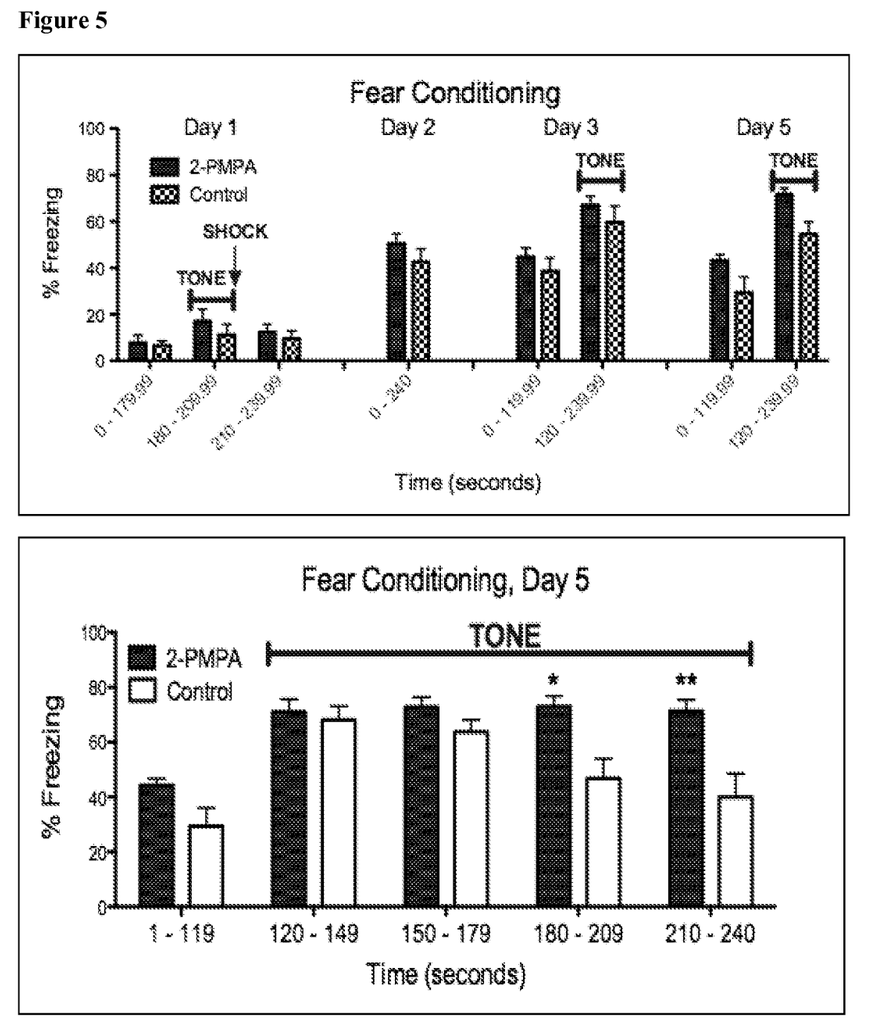
FIG. 5 shows the results of a 5 day fear conditioning test that was conducted following Barnes maze testing. EAE mice received a tone paired with a footshock on the first day of testing. Contextual memory was tested on day 2, and cued memory was tested on days 3 and 5. On day 5, 2-PMPA treated mice froze more than Controls in response to the tone, indicating an improvement in memory retention. Values represent the mean±SEM of % time freezing in the chamber. n=10 mice/group. Significantly different from Control at p<0.05 (*) or p<0.01(**).

2-PMPA and control EAE mice demonstrated equally low baseline freezing (<20%) on Day 1. Contextual freezing on Day 2 was equal between 2-PMPA (Mean±SEM: 50.49±4.18) and control (Mean±SEM: 42.61±5.63) mice. No differences in cued freezing behavior were observed between groups on Day 3. On Day 5, however, mice treated with 2-PMPA had increased cued freezing in response to the 120 second tone, specifically in the last 60 seconds, indicating a stronger fear memory in 2-PMPA-treated EAE mice compared to control mice (FIG. 5).

To confirm that the differences observed in fear conditioning performance were due to differences in fear memory and not anxiety, elevated plus maze tests were conducted. A separate cohort of 2-PMPA and Control EAE mice (n=6-7) were tested on the elevated plus maze 27 days after disease induction. Mice were placed in the center of the maze and given 5 minutes to freely explore the maze. Time spent in open and closed arms of the maze were tracked using ANY-maze software (Stoelting, Wood Dale, Ill.). No differences were noted between 2-PMPA and Control groups regarding the time spent in the open arms (Mean±SEM: 34.10±9.22 vs. 35.90±6.99, respectively) and closed arms (Mean±SEM: 224.2±10.07 vs. 225.6±13.65, respectively) of the maze, indicating equal anxiety levels.

Example 3: Reduced NAAG Levels in the Frontal Cortex in Mice Treated with a GCPII Inhibitor To determine whether GCPII inhibition altered the levels of the enzyme's substrate (NAAG) or product (NAA), mass spectrometry was conducted in post-mortem brains of EAE mice either treated with 2-PMPA or a vehicle control. Animals were sacrificed by cervical dislocation 50 days after EAE immunization. Hippocampus, frontal lobe, and cerebellum structures were dissected, and NAA, NAAG, and 2-PMPA concentrations were measured via mass spectrometry. Briefly, NAAG and NAA in brain tissue homogenates were separated on a Waters Atlantis ODS column. NAA, NAAG, and the internal standard were monitored by tandem mass spectrometry with electrospray negative ionization. Linear calibration curves were generated over the range of 5-5000 ng/mL and converted to µg/g. For determination of 2-PMPA, separations were achieved on a Waters XTerra MS C18 column. 2-PMPA and the internal standard were monitored by tandem mass spectrometry with electrospray negative ionization. Linear calibration curves were generated over the 1-100 ng/mL range and converted to µg/g.

Figure 6:
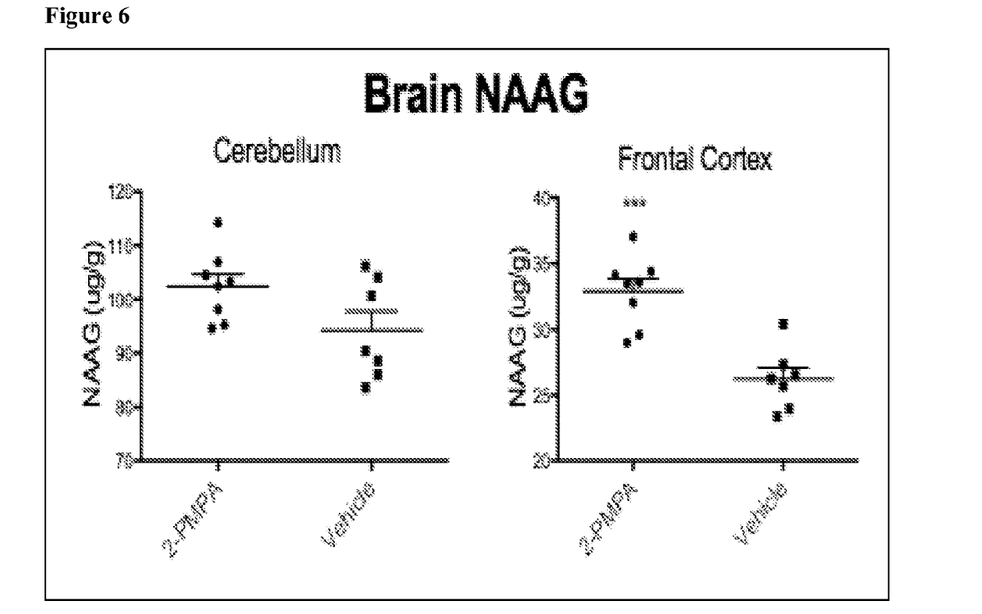
FIG. 6 shows that EAE mice treated with 2-PMPA had increased brain NAAG levels compared to Control EAE mice. Values represent mean±SEM. n=8 mice/group. Significantly different from Control at p<0.001(***).
Figure 7:
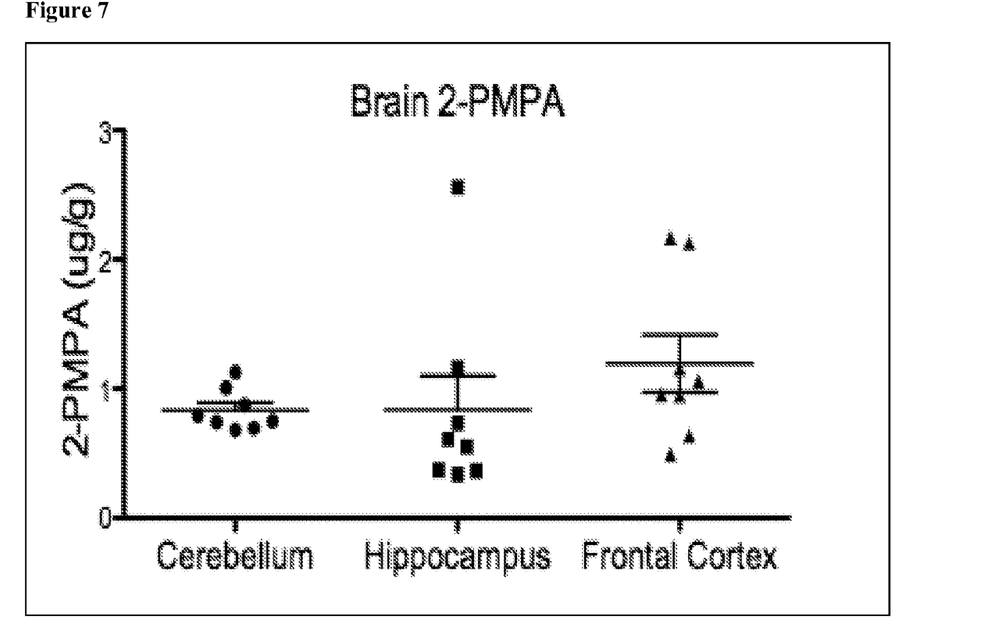
FIG. 7 shows that EAE mice treated with 2-PMPA had measurable levels of the drug in all areas of the brain tested, including the cerebellum, hippocampus, and frontal cortex. Values represent ug 2-PMPA per g brain tissue, mean±SEM. n=8 mice/group.

Brain analysis of NAA showed no differences between 2-PMPA (n=8) and control (n=7) mice in the hippocampus (Mean±SEM: 985.0±48.12 vs. 1075±67.3, respectively; p=0.2895), cerebellum (Mean±SEM: 899.3±19.66 vs. 844.1±50.82, respectively; p=0.3053), and frontal cortex (Mean±SEM: 1134±45.65 vs. 1049±67.01, respectively; p=0.3035). 2-PMPA treatment did not affect NAAG concentration compared to controls in the hippocampus (Mean±SEM: 54.98±2.037 vs. 55.54±2.275, respectively; p=0.8575), caused a trend in increased NAAG concentration compared to controls in the cerebellum (Mean±SEM: 102.4±2.3 vs. 94.23±3.5, respectively; p=0.0655), and significantly increased NAAG concentration compared to controls in the frontal cortex (Mean±SEM: 32.91±0.93 vs. 26.22±0.8727, respectively; p=0.0002) (FIG. 6). 2-PMPA was detected in all brain regions of 2-PMPA treated mice, including the cerebellum (Mean±SEM: 0.832±0.056 ug/g tissue), hippocampus (Mean±SEM: 0.835±0.264 ug/g tissue), and frontal cortex (Mean±SEM: 1.193±0.222 ug/g tissue) (FIG. 7).

We claim:

1. A method of treating cognitive impairment in a subject who has multiple sclerosis (MS), the method comprising the steps of:
(a) performing magnetic resonance spectroscopy (MRS) to detect a concentration of N-acetylaspartylglutamate (NAAG) in the brain of the subject that is less than 84% of the mean NAAG concentration in the brain of a healthy subject, or a concentration of NAAG in a region of the brain of less than 3.1 mM in the hippocampus or less than 1.9 mM in the frontal white matter; and
(b) administering to the subject an inhibitor of glutamate carboxypeptidase II (GCPII).

2. The method of claim 1, wherein the concentration of NAAG in the brain of the subject is less than 84% of the mean NAAG concentration in the brain of a healthy subject.

3. The method of claim 1, wherein the concentration of NAAG in a region of the brain of the subject is less than 3.1 mM in the hippocampus.

4. The method of claim 1, wherein the concentration of NAAG in a region of the brain of the subject is less than 1.9 mM in the frontal white matter.

5. The method of claim 1, wherein the inhibitor of GCPII is an acid linked to a zinc binding group or a NAAG peptide analog.

6. The method of claim 1, wherein the inhibitor of GCPII is 2-(phosphonomethyl) pentanedioic acid (2-PMPA) or 2-(3-mercaptopropyl)pentanedioic acid (2-MPPA).

7. The method of claim 6, wherein the inhibitor of GCPII is 2-PMPA.

8. The method of claim 6, wherein the inhibitor of GCPII is 2-MPPA.

* * * * *